United States Patent [19]
Pearson

[11] 3,988,369
[45] Oct. 26, 1976

[54] PROCESS AND REACTANT FOR HALOGENATING ORGANIC COMPOUNDS

[76] Inventor: Donald E. Pearson, 112 Clydelan Court, Nashville, Tenn. 37205

[22] Filed: Sept. 26, 1974

[21] Appl. No.: 509,511

[52] U.S. Cl. .................. 260/544 R; 260/590 FB; 260/543 R; 260/600 A; 260/586 R; 260/623 H; 260/648 C; 260/648 R; 260/649 R; 260/650 R; 252/182
[51] Int. Cl.$^2$ .................. C07B 9/00; C07C 17/00
[58] Field of Search ............... 260/695 R, 544 A-L, 260/660, 648 R, 544, 649 R, 600, 623 H, 650 R, 590; 252/182

[56] References Cited
UNITED STATES PATENTS

| | | | |
|---|---|---|---|
| 3,088,917 | 5/1963 | Friedman et al. | 252/182 |
| 3,668,154 | 6/1972 | Buisson | 252/182 |
| 3,763,250 | 10/1973 | Rai et al. | 260/648 R |

*Primary Examiner*—Lewis Gotts
*Assistant Examiner*—Cary Owens
*Attorney, Agent, or Firm*—John W. Carpenter

[57] ABSTRACT

A process and solvent and/or reactant for halogenating organic compounds. The organic compounds are contacted with a solution of trialkyl phosphate and a halogen. The solution of trialkyl phosphate may additionally include phosphorous pentoxide.

9 Claims, No Drawings

PROCESS AND REACTANT FOR HALOGENATING ORGANIC COMPOUNDS

BACKGROUND OF THE INVENTION

1. Field of the Invention

This invention is related to a process and reactant for halogenating. More specifically, this invention provides a process and solvent and/or reactant for halogenating organic compounds.

2. Description of the Prior Art

U.S. Pat. No. 3,763,250, patented Oct. 2, 1973, by Rai, Marcellis and Pearson, will be incorporated by reference and discloses a novel process for halogenating organic compounds under mild conditions utilizing a halogen system comprising halogen in a solution of phosphorus pentoxide in trimethyl phosphate. Prior to the conception of this invention I had invented the halogenating solvent and/or reactant which is the subject matter of this application. Prior to my discovery, halogenating of organic compounds could only be accomplished under high temperature and pressure conditions, as well as long reaction times with/and without the use of free radical initiators, high intensity light or electrophilic catalysts. These reactions are often difficult to control (e.g. liberated mixtures of chlorine and gaseous hydrocarbons such as methane may explode when irradiated by ultraviolet light).

Convention halogenation of organic compounds also has the disadvantages of generating hydrogen halide as a reaction byproduct when free halogen is used as the halogenating reagent to replace hydrogen on a carbon of an organic compound. The generation of hydrogen halide precludes the use of ferrous reaction equipment wherever such equipment may come in contact with the hydrogen halide and precludes the halogenation of an organic compound which is sensitive to the presence of hydrogen halide.

SUMMARY OF THE INVENTION

It is therefore an object of this invention to provide a process and reactant for halogenating organic compounds.

It is another object of this invention to provide a process and reactant for halogenating organic compounds that causes relatively rapid halogenation of organic compounds under mild reaction conditions.

It is yet another object of this invention to provide an economical process and reactant that will cause the replacement by halogen of at least one hydrogen on a saturated carbon of an organic compound, such as a cycloparaffin or at least one hydrogen attached to an aromatic nucleus, without the evolution of by-product hydrogen halide.

Still other objects and advantages of this invention will be apparent to those skilled in the art from the following description of this invention.

The foregoing objects are achieved in accordance with this invention. Broadly, this invention provides a solvent and/or reactant for halogenating organic compounds comprising a trialkyl phosphate and a halogen wherein the mole ratio of the trialkyl phosphate to halogen is from about 1:1 to about 1:100. The solvent and/or reactant may additionally include phosphorus pentoxide wherein the mole ratio of the solution of phosphorus pentoxide to trialkyl phosphate to halogen is from about 0.001:1 to about 1:1. This invention also provides a process for halogenating organic compounds comprising contacting the organic compound with the solvent and/or reactant as was previously defined at a temperature of from about 0° to about 150° C.

Thus, by practicing the present invention it is possible to have a reactant which causes rapid halogenation of organic compounds under mild reaction conditions. Utilization of the reactant in halogenation process of this invention makes unnecessary the employment of radical initiators, actinic radiation, or electrophilic catalysts. Also, the halogenation reaction is easily controlled. In the process of this invention where hydrogen on a saturated or unsaturated carbon of an organic compound is replaced by halogen, there is no evolution of by-product hydrogen halide.

DETAILED DESCRIPTION OF THE INVENTION

The process of this invention for halogenating organic compounds broadly comprises contacting or dissolving the organic compounds with a trialkyl phosphate and a halogen. The trialkyl phosphate may be any suitable trialkyl phosphate; however, a preferred trialkyl phosphate is one selected from the group consisting of trimethyl phosphate, triethyl phosphate, tripropyl phosphate and tributyl phosphate including the branched chain esters. A more preferred trialkyl phosphate is selected from trimethyl phosphate and triethyl phosphate; the most preferred trialkyl phosphate is trimethyl phosphate. The halogen may also be any suitable halogen but in a preferred embodiment is one selected from the group consisting of chlorine, bromine, and iodine. The organic compounds which are contacted may be any suitable organic compounds (e.g. hydrocarbons, phenols, ketones, acid chlorides, etc.) but is preferably an aromatic based compound such as a cycloparaffin selected from the group consisting of cyclopentane, cyclohexane, and cycloheptane or an aromatic compound selected from a group of benzene, phenol, fluorenone or similar species.

The mole ratio of the trialkyl phosphate to the halogen may broadly be from about 1:1 to about 1:100. The more preferred mole ratio range of the trialkyl phosphate to the halogen is from between about 50 to about 1; most preferably, the mole ratio is from between about 12 to about 8.

The trialkyl phosphate may additionally include phosphorus pentoxide wherein the mole ratio of phosphorus pentoxide to halogen is from between about a negligible amount (e.g. 0.001):1 to about 3:1. The phosphorus pentoxide serves a purpose with those substrates containing a group which reacts with phosphorus pentoxide. Generally, however, the phosphorus pentoxide serves no useful purpose and may be eliminated unless a group is present which reacts with it in a desirable manner.

The reaction temperatures of my process are generally within the range of about 0° to about 150° C, and preferably within the range of about 8° to about 100° C. Most preferred is a temperature range of from between about 25° to about 50° C. I generally employ atmospheric pressure in my invention; however, it should be understood that greater than atmospheric pressure may be used when elevated temperatures are employed. Reaction pressures should broadly be in the range of from between about 1 to 8 atmospheres with the more preferred pressures being about 1 to 2 atmospheres.

The process of this invention is useful for halogenating classes of organic compounds that are difficult to halogenate by other methods or at the very least is capable of improving yields. The process of this invention has its greatest utility in the halogenation of cycloparaffinic hydrocarbons and aromatic compounds and, as was mentioned in U.S. Pat. No. 3,763,250, in the halogenation of acyl halides having an alpha-hydrogen. Both of the foregoing halogenation reactions involve replacement by halogen of hydrogen on a saturated or unsaturated carbon. The process has the added advantage that the trialkyl phosphate reacts with by-product hydrogen halides to form the corresponding alkyl halide. The corresponding alkyl halide, unlike the hydrogen halide, is non-corrosive and is a valuable by-product of the reaction, thereby improving the overall economics of the process. The trialkyl phosphate gives in some cases a different product than normal media such as acetic acid. In other cases, the trialkyl phosphate may give a product where the normal medium will not; in such cases, the halogen substitutes into the medium (such as acetic acid) rather than into the substrate. Additional advantages of the instant process and solvent and/or reactant are that the process utilizing the solvent is carried out under mild reaction conditions; it proceeds relatively rapidly; and neither free radical initiators nor actinic radiation nor electrophilic catalysts are required.

In the following is set forth examples of my invention which are given by way of illustration and not by limitation. The specific concentrations, temperatures, times, compounds, etc., set forth in these examples are not to be construed to unduly limit the scope of the invention.

EXAMPLE I

To 5 g of 9, 10-dihydrophenanthrene in 30 ml of trimethyl phosphates (TMP), stirred magnetically, was added dropwise 9.5 g of bromine dissolved in 20 ml of TMP. The separatory funnel and reaction vessel were protected from light, and all precautions were taken to keep apparatus and reagents free of moisture. After addition a solid began to form but it was stirred overnight for about 12 hours (temperature was circa 35° C). The mixture was chilled in the refrigerator (at about 5° C for about 8 hours); the cream-colored solid was washed with cold alcohol and recrystallized from chloroform to yield cream-colored crystals, 13.8 g in 3 crops, 55%, mp 163°–165.5° C. Calcd for $C_{14}H_{10}Br_2$: % wt. Br, 47.28: Found: % wt. Br, 47.67. To prove the compound had the correct structure, it was brominated and dehydrobrominated by NBS in $CCl_4$ under irradiation. 2,7-Dibromophenanthrene was obtained, mp 200°–202° C, reported (in Heibron, Dictionary of Organic Compounds) mp 200° C.

EXAMPLE II

Chlorine gas was bubbled through 30 ml of TMP at near 0° C until 5.1 g of chlorine had dissolved. This solution was added dropwise to a magnetically stirred solution of 5 g of fluorene in 50 ml of TMP at 45° C. After addition was complete, the temperature was raised slowly to 100° C and held there until a chlorine test was negative (starch-iodide paper). Poured into 100 ml of ice water and extracted the solid 3 times with hexane, the yellow residue from hexane was recrystallized twice from alcohol to give 4.2 g, 60%, of 2,7-Dichlorofluorene, mp 119°–121° C, literature (F. Dewhurst, P. K. J. Shah, *J. Chem. Soc.*, C, 1737 (1970)) mp. 126° C after repeated recrystallization.

EXAMPLE III

Example performed identical to Example II but with the addition of 11.5 g of phosphorus pentoxide to the TMP. Yield of 2,7-Dichlorofluorene: 2.9 g, 50%, mp 120°–122° C.

EXAMPLE IV

Iodine monochloride (10 g) was dissolved in 30 ml of TMP with cooling. Considerable heat evolved. This solution was added dropwise to a solution of 5 g of fluorene in 30 ml TMP stirred, held at 83°–100° C overnight (about 12 hours), refrigerated (at 5° C for about 6 hours) and filtered to give 4.8 g of white, fine needles. Another 2.4 g was recovered from filtrate - total crude yield 60%. Recrystallized from tetrahydrofuran to which a few (2) ml of ethyl alcohol was added 2,7-Diiodofluorene was obtained: 5.6 g, 44% of white needles, mp 214°–215°, reported (in F. Dewhurst, P. K. J. Shah, *J. Chem. Soc.*, 1503 (1969)) mp 214° C.

EXAMPLE V

Triethyl phosphate was used as the reacting solvent in place of TMP, otherwise conditions were the same as Example II except that an extra 24 hours of stirring at 85° C was employed. There was obtained 2 g, 16% of 2,7-Diiodofluorene and 1.4 g, 28% of fluorene.

Thus, it was shown that trimethyl phosphate is a better reacting solvent than triethyl phosphate. Trimethyl phosphate was found to be unique as being the only non-acidic solvent which dissolves phosphorus pentoxide. Also, the workup of the products from halogenation in TMP is simplified because TMP dissolves readily in water and the product can be diluted out of TMP by water. In addition, TMP is not soluble in hexane. If ether is used, a wash or two of the ether by water is desirable. The insolubility of TMP in hexane also permits extraction of the TMP by hexane without dilution of TMP by water. This can be advantageous in processes where it is desirable to recover the TMP.

EXAMPLE VI

Reaction was carried out on vanillin as in Example II except that one equivalent of chlorine was used and the temperature was held at 8°. On dilution, the product crystallized out to give 64% of 5-chlorovanillin, mp 167°–166°. The reported mp is 164°–166° and it was made from vanillin, t-butylhypochlorite in acetic acid, t-butyl alcohol or carbon tetrachloride in 81–84% yields (D. Ginsberg, *J. Amer. Chem. Soc.*, 73, 703 (1951)).

EXAMPLE VII

5-Bromovanillin was prepared similarly to that in Example I. Carried out at 55° for 18 hours there was obtained after recrystallization from aqueous methanol 5 g, 72% of pale yellow crystals, mp 161°–163°. The reported mp is 162°–164° and was obtained by bromination in acetic acid starting at room temperature (F. Misani, M. T. Bogert, *J. Org. Chem.*, 10, 356 (1945)).

EXAMPLE VIII

Preparation of 3-Chloro-4-Dichloromethyl-2, 6-di-t-butylphenol. To 0.02 ml of 2,6-di-t-butyl-4-cresol in 75 ml of TMP dropwise in 2 hours at 30°. The mixture was allowed to stand overnight and heated the next day at 50° for 6 hours. Even though a trace of chlorine was still present, the mixture was poured into water and extracted with hexane. The residue (6.15 g) from hexane evaporation partly crystallized and the crystals could be separated from the yellow oil by washing with hexane and decanting. The crystals, 0.9 g, were recrystallized from hexane, giving transparent needles, mp 176°–177°. The nmr was unequivocal: δ 1.12, s, 9, C(CH$_3$)$_3$; 1.3, s, 9, C(CH$_3$)$_3$; 5.2, s, 1, OH; 6.55, s, 1, CHCl$_2$; 7.22, s, 1, aromatic H.

Anal. Calcd for C$_{15}$H$_{21}$Cl$_3$O: Cl, 32.86. Found: Cl, 32.63. This product is the first example in which a halogen atom has been inserted into the aromatic ring of 2,6-di-t-butyl-4-cresol. The compound is quite stable compared to 2,6-di-t-butyl-4-cresol and might be an effective antioxidant where the di-t-butylcresol fails.

EXAMPLE IX

Preparation of Bromo-1,3,5-tri-t-butylbenzene. Bromine (2.4 g, 0.015 mole) was added to a mixture of 16 g of phosphorus pentoxide (which could be left out) and 2.5 g, 0.01 mole of tri-t-butylbenzene and the mixture warmed at 60°–65° for 24 hours. Some precipitate had formed but the entire mixture was poured into water. The white precipitate was filtered and dried, 3.1 g, 95% crude. It was crystallized from 60 ml of alcohol to give 1.9 g, 59% of beautiful, white platlets, mp 170°–172°. Nmr was compatible, and literature mp was 177°–177.5° (E. E. Batts, L. R. C. Barclay, *Can. J. Chem.*, 33, 1768 (1958)). It was made previously by brominating tri-t-benzene in acetic acid using bromine and silver nitrate (yield 50%).

EXAMPLE X

Bromination of tri-t-butylbenzene in acetic acid. The reaction was carried out very similarly to Example IX except that acetic acid was substituted for TMP. The reaction mixture was held at 75°–80° until chlorine had disappeared (49 hours). There was a quantitative recovery of crude solid which on recrystallization from ethanol, gave 1.9 g, 76% of white needles, mp 72°–74.5° which is the mp of tri-t-butylbenzene.

EXAMPLE XI

Preparation of 2,7-Dibromofluorenone. To a stirred solution of fluorenone, 0.07 mole, in 150 ml of TMP was added 25 g (0.16 mole) of bromine in 50 ml of TMP in 30 min. and the mixture maintained at 90° for 42 hours, cooled, poured into cold water (temp. circa 10° C) and treated with a little sodium bisulfite to remove excess bromine. The yellow precipitate was filtered, washed with water, and recrystallized from acetic acid to give yellow needles, 17 g, 70% mp 201°–203°, literature (I. M. Heilbron, Dictionary of Organic Compounds, Vol. II, 1965, p. 924) mp 202°.

EXAMPLE XII

Preparation of 4-Iodo-2-Cresol: 0-Cresol, 0.023 ml, iodine, 3 g, and 25 ml of trimethyl phosphate were held at 87° C under nitrogen for 12 hours with stirring. The iodine color having disappeared, 2.9 g more of iodine (total iodine 0.023 mol) was added and held 12 hours again. The iodine was gone but a brown color had developed. The mixture was poured into water and extracted with hexane. Three layers formed: the hexane layer containing the product, a dark viscous oil at interface of hexane, and water (which was a phosphate ester of product) the aqueous layer. The hexane layer was separated, dried and evaporated. The residue, 5 g, contained about 60% of the desired product (GLC, RT=108 sec. on 6 ft. SE 30 column at 150° and 40 ml of He/min. flow) and 40% trimethyl phosphate (40%, RT=60 sec.). There were indications of less than 1% 6-iodo-2-cresol (RT=112 sec.) and about 1% 4,6-diiodo-2-cresol (RT=180 sec.). This crude mixture was warmed on a steam-bath with 8% aqueous sodium hydroxide, cooled, acidified, and the solid obtained filtered and washed. The same treatment was given to the heavy oil insoluble in hexane. The crude weight of 4-iodo-2-cresol obtained in this way were 3.5 g, 65% and 0.35 g, 6%, respectively. Recrystallization of first fraction gave shiny, beige-colored needles, mp 66.5°–68° (colorless melt), 1.55 g, 29% reported (C. M. Suter, R. D. Shultz, *J. Org. Chem.*, 16, 1117 (1951)) mp 64°–65°. The second crop from the filtrate combined and recrystallized with the 0.35 g fraction gave 1.1 g, 20%, of darker beige needles, mp 65°–67° (amber melt).

EXAMPLE XIII 0.1 mol of substrate is dissolved in 60 ml of trimethyl phosphate, treated with 0.1 mol of iodine, and heated until bromine disappears. Part of the methyl iodide is trapped in a receiver cooled in ice-salt if reaction is carried out at elevated temperatures (80°). The reaction vessel originally was the pot for distillation, This pot was attached to a vacuum apparatus with short Vigriux column. The receiver was cooled in dry ice-acetone and water pressure vacuum applied. The rest of the methyl iodide was collected in this way except for some loss through evaporation. After the methyl iodide had been collected, the apparatus was connected to a high vacuum pump (0.1 – 1 ml pressure, and the pot slowly heated until trimethyl phosphate came over dropwise (bp 35°–50°) depending on pressure. The yield of TMP was almost quantitative except for that utilized in forming methyl iodide. The residue was poured into water, filtered, and washed free of acid, and recrystallized from appropriate solvent to give the desired iodo compound.

EXAMPLE XIV 64 g of P$_2$O$_5$ was dissolved in 150 ml of trimethyl phosphate and 100 ml of ethylene chloride. To this solution 0.1 mole of phenanthrene was added followed by 0.22 mol of bromine. The mixture was held 9 hours at 50°–60° and on cooling gave 35 g (thero. =33.6) of mixed polybromophenanthrenes. The 35 g was rebrominated in the same manner as above. On cooling the product crystallized out. The yield was 21 g which in crystallization from ethylene chloride gave yellow, brittle clumps, 6.1 g, mp 117°–121°, clears at 124°–130°). Mass spectrometry indicates a mixture of mostly tribromophenanthrene with traces of tetrabromophenanthrene. The material from filtrate was rebrominated with aluminum chloride. This is a more drastic bromination. It could not have been done starting with phenanthrene because phenanthrene with aluminum chloride turns black indicating partial polymerization. 14 g of the tribromophenanthrene, crude, was dissolved in 140 ml of tetrachloroethylene, 1 g of Al$_2$Cl$_3$ added, and then 8.5 g (0.053) mol and the mixture held at 60°–63° for 2 hours. The product was poured into water and the solid filtered and washed with water. Recrystallization from ethylene chloride gave 2.8 g of solid insoluble in ethylene chloride which recrystallized from chlorobenzene to give 0.7 g, silky crystals, mp 308°–310°, mass spec. indicated a hexabromophenanthrene. Ignition shows that this compound chars but does not maintain its own combustion and greenish vapor. The product from ethylene chloride was sublimed at 0.1 mp to give white crystals, mp 256°–258° (clears to 270°, a total of 7 g (DP-7 pg. 14, 15, 16). This compound melts on ignition but does not burn.

EXAMPLE XV

Halogenic variations of the compounds of Examples I–XI are prepared similarly to the Examples but varying the halogen (chlorine, bromine, iodine) and the trialkyl phosphate (TMP, triethyl phosphate, tripropyl phosphate, tributyl phosphate, etc.). Also, phosphorus pentoxide is added to the particular trialkyl phosphate to determine its effectiveness on the results. For each Example it is found that the resulting compound was equivalent in structure and properties to that in the literature, depending on the halogen utilized.

Thus, by the practice of this invention, it is found that trialkyl phosphates are solvents and/or reactants of unusual properties for halogenation of organic compounds, and hydrogen halide is not liberated in halogenation reactions with trialkyl phosphates. Trimethyl phosphate is found to be particularly useful among the trialkyl phosphates for halogenation because halogenation reactions are more complete in a given amount of time. Trimethyl phosphate halogenation can be run in the presence of phosphorus pentoxide even though the yield may be somewhat lower. In certain cases, as aforementioned, it may be necessary to have phosphorus pentoxide present to obtain a desired product. Halogenation in trialkyl phosphates are superior to halogenations in other media when the substrate is a substance or intermediate which tends to polymerize (polynuclear hydrocarbons, heterocycles) or which tends to disproportionate or to lose groups (phenols or other activated aromatics with tert or sec alkyl groups).

While the present invention has been described herein with reference to particular embodiments thereof, and specific examples, a latitude of modifications, various changes and substitutions are intended in the foregoing disclosure, and in some instances some features of the invention will be employed without a corresponding use of other features without departing from the scope of the invention as set forth.

I claim:
1. A reactant comprising a trialkyl phosphate wherein the alkyl radical has 4 or less carbon atoms and a halogen selected from the group consisting of chlorine, bromine and iodine, wherein the mole ratio of trialkyl phosphate to halogen is from about 1:1 to about 1:100.

2. The reactant of claim 1 additionally including phosphorus pentoxide wherein the mole ratio of the solution of phosphorus pentoxide in trialkyl phosphate to halogen is from about 0.001:1 to about 3:1.

3. A process for halogenating organic compounds comprising contacting said organic compounds with a trialkyl phosphate wherein the alkyl radical has 4 or less carbon atoms and a halogen selected from the group consisting of chlorine, bromine and iodine, wherein the mole ratio of trialkyl phosphate to halogen is from about 1:1 to about 1:100 and the halogenation is carried out at a temperature of from about 0° to about 150° C.

4. The process of claim 3 additionally including adding phosphorus pentoxide wherein the mole ratio of the solution of phosphorus pentoxide in trialkyl phosphate to halogen is from about 0.001:1 to about 3:1.

5. The process of claim 4 wherein said organic compounds include cycloparaffins.

6. The process of claim 5 wherein said organic compounds include aromatic hydrocarbons.

7. The process of claim 6 wherein said organic compounds include phenols.

8. The process of claim 7 wherein said organic compounds include ketones.

9. The process of claim 8 wherein said organic compounds include acid chlorides.

* * * * *